(12) United States Patent
Kubo et al.

(10) Patent No.: US 9,591,992 B2
(45) Date of Patent: Mar. 14, 2017

(54) METHOD OF EXHALED GAS MEASUREMENT AND ANALYSIS AND APPARATUS THEREFOR

(75) Inventors: Yasuhiro Kubo, Konan (JP); Masaaki Mori, Hirakata (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 813 days.

(21) Appl. No.: 13/565,437

(22) Filed: Aug. 2, 2012

(65) Prior Publication Data

US 2014/0194765 A1 Jul. 10, 2014

Related U.S. Application Data

(62) Division of application No. 12/223,539, filed as application No. PCT/JP2007/051590 on Jan. 31, 2007, now abandoned.

(30) Foreign Application Priority Data

Feb. 3, 2006 (JP) .................................. 2006-027365

(51) Int. Cl.

| | |
|---|---|
| *A61B 5/08* | (2006.01) |
| *A61B 5/083* | (2006.01) |
| *G01N 1/22* | (2006.01) |
| *G01N 21/3504* | (2014.01) |
| *G01N 33/497* | (2006.01) |
| *A61B 5/097* | (2006.01) |

(52) U.S. Cl.
CPC ............ *A61B 5/0836* (2013.01); *A61B 5/097* (2013.01); *G01N 1/22* (2013.01); *G01N 21/3504* (2013.01); *G01N 33/497* (2013.01)

(58) Field of Classification Search
CPC .............................. A61B 5/0836; A61B 5/097
USPC .................................................... 600/529–534
See application file for complete search history.

(56) References Cited

U.S. PATENT DOCUMENTS 3,238,783 A    3/1966 Wright
4,313,445 A *  2/1982 Georgi ............... A61B 5/02208
                                                  600/493

(Continued)

FOREIGN PATENT DOCUMENTS

EP    0 953 148 B1    11/1999
JP    44-3554          2/1969

(Continued)

OTHER PUBLICATIONS

Form PTO-892 issued in Office Action in U.S. Appl. No. 12/223,539.

(Continued)

*Primary Examiner* — Tiffany Weston
(74) *Attorney, Agent, or Firm* — Finnegan, Henderson, Farabow, Garrett & Dunner, L.L.P.

(57) ABSTRACT

An exhalation collected in a breath bag capable of expanding and contracting is sucked into a gas inlet vessel 21 with a given volume (Va), and then the gas inlet vessel 21 is communicated by means of valve V2 with a cell 11 that is maintained at an atmospheric pressure by being pre-filled with a sample gas or reference gas. After the communication, the gas pressure is measured by a pressure sensor 16 attached to the cell 11. Whether the exhalation collected in the breath bag is below a given amount or not can be accurately judged.

1 Claim, 8 Drawing Sheets

(56) References Cited

U.S. PATENT DOCUMENTS

| | | | |
|---|---|---|---|
| 5,964,712 A * | 10/1999 | Kubo et al. | 600/529 |
| 6,940,083 B2 | 9/2005 | Mori et al. | |
| 7,063,667 B1 | 6/2006 | Ben-Oren et al. | |
| 2003/0178589 A1* | 9/2003 | Mori et al. | 250/573 |
| 2005/0177057 A1 | 8/2005 | Friedman et al. | |
| 2009/0306527 A1 | 12/2009 | Kubo et al. | |

FOREIGN PATENT DOCUMENTS

| | | |
|---|---|---|
| JP | 53-42890 | 4/1978 |
| JP | 06-84345 A | 12/1994 |
| JP | 09-15248 | 1/1997 |
| JP | 10-197443 | 7/1998 |
| JP | 10-197445 | 7/1998 |
| JP | 11-76202 | 3/1999 |
| JP | 2002-98629 | 4/2002 |
| JP | 2005-3387 | 1/2005 |
| WO | WO 97/14029 A2 | 4/1997 |
| WO | WO 98/30888 A1 | 7/1998 |
| WO | WO 00/72754 | 12/2000 |
| WO | WO 02/25250 A2 | 3/2002 |
| WO | WO 2005/041769 * 5/2005 ............. A61B 5/083 |
| WO | WO 2005/041769 A1 | 5/2005 |

OTHER PUBLICATIONS

European Patent Office, "Supplementary European Search Report." Aug. 26, 2013, 6 pp., Appilcation No. EP 07 71 3750, Munich, Germany.

* cited by examiner

METHOD OF EXHALED GAS MEASUREMENT AND ANALYSIS AND APPARATUS THEREFOR

RELATED APPLICATIONS

This application is a divisional of U.S. application Ser. No. 12/223,539 filed Dec. 1, 2008 now abandoned, which is a §371 of International Application No. PCT/JP2007/051590, filed Jan. 31, 2007, which claims priority to Japanese application Ser. No. 2006-027365, filed Feb. 3, 2006, the contents of all of which are incorporated herein by reference.

TECHNICAL FIELD

Isotopic analyses are utilized for diagnosis of diseases in medical field, in which metabolic functions of a living body can be determined by administering an isotope-containing drug to the living body and then detecting a change in the concentration ratio of the isotopes.

The present invention relates to a method of exhaled gas measurement and analysis and an apparatus for measuring the concentration of carbon dioxide $^{13}CO_2$, or the concentration ratio of $^{13}CO_2$ to $^{12}CO_2$ in a human exhalation based on a difference in light absorption characteristic between isotopes.

BACKGROUND ART

The bacteria called *Helicobacter Pylori* (HP) are generally known as a cause of gastric ulcers and gastritis.

If the HP is present in the stomach of a patient, an antibiotic or the like should be administered to the patient for bacteria removal treatment. Therefore, it is important to check if the patient has the HP. The HP has a strong urease activity for decomposing urea into carbon dioxide and ammonia.

Carbon has isotopes having mass numbers of 12, 13 and 14, among which $^{13}C$ having a mass number of 13 is easy to handle because of its non-radioactivity and stability.

If the concentration of $^{13}CO_2$ as a final metabolic product in breath of the patient, more specifically, a $^{13}CO_2/^{12}CO_2$ concentration ratio, can successfully be determined after $^{13}C$-labeled urea is administered to the patient, the presence of HP can be confirmed.

However, the concentration ratio of $^{13}CO_2$ to $^{12}CO_2$ in naturally occurring carbon dioxide is 1:100, making it difficult to accurately determine the concentration ratio in the breath of the patient.

There have been known methods for determining the concentration ratio of $^{13}CO_2$ to $^{12}CO_2$ or the concentration of $^{13}CO_2$ by way of infrared spectrophotometry (see Japanese Unexamined Patent Publication No. 53-42890 (1978)).

In the method disclosed in Japanese Unexamined Patent Publication No. 53-42890, two cells respectively having a long path and a short path are prepared. The path lengths of the cells are adjusted such that a $^{13}CO_2$ absorbance in one of the cells is equalized to a $^{12}CO_2$ absorbance in the other cell. Light beams having wavelengths suitable for the respective analyses are applied to the respective cells, and the intensities of transmitted light beams are measured. According to this method, an absorbance ratio for the concentration ratio in naturally occurring carbon dioxide can be set at 1. Therefore, the absorbance ratio is changed correspondingly to a change in the concentration ratio. This allows detection of the change in the concentration ratio.

Patent Document 1: Japanese Unexamined Patent Publication No. 53-42890 (1978)
Patent Document 2: Japanese Unexamined Patent Publication No. 2002-98629
Patent Document 3: International Publication No. WO1997/14029 Pamphlet
Patent Document 4: International Publication No. WO1998/30888 Pamphlet
Patent Document 5: International Publication No. WO2002/25250 Pamphlet
Patent Document 6: International Publication No. WO2005/41769 Pamphlet

DISCLOSURE OF THE INVENTION

Problems to be Solved by the Invention

Where the foregoing infrared spectrophotometry is adopted, if the amount of breath obtained from a patient is below a predetermined amount, the reliability of the measured data deteriorates.

Therefore, at present, whether the amount of breath is adequate or not is judged by visually observing the profile of the breath bag. Since the breath bag is flexible, whether it is filled up with the breath can be judged by its profile.

However, whether the amount of breath is more or less than the foregoing predetermined amount or how much less than the predetermined amount cannot be determined accurately by such a visual observation.

Therefore, it is an object of the present invention to provide a method of exhaled gas measurement and analysis and an apparatus used where an exhalation including carbon dioxide $^{13}CO_2$ and carbon dioxide $^{12}CO_2$ as component gases is introduced into a cell for measuring the concentrations of the respective component gases by infrared spectrophotometry, which are capable of accurately determining whether the obtained breath is less than the predetermined amount or not so as to prevent output of erroneous data.

Means for Solving the Problems

A method of exhaled gas measurement and analysis according to the present invention comprises the steps of: collecting an exhalation of a human body including carbon dioxide $^{13}CO_2$ and carbon dioxide $^{12}CO_2$ as component gases into a breath bag capable of expanding and contracting; sucking a predetermined volume of the exhalation collected in the breath bag into a gas inlet vessel; measuring the pressure of the exhalation in the gas inlet vessel; cancelling the measurement upon determining that the amount of the exhalation collected in the breath bag is insufficient when the measured pressure value is below an atmospheric pressure; pushing the gas inlet vessel to fill a cell with the exhalation when the measured pressure value is equal to the atmospheric pressure; and measuring the intensities of light transmitted through the cell having wavelengths at which light is transmitted through the respective component gases, followed by data processing based thereon, thereby measuring concentration of $^{13}CO_2$ or concentration ratio of carbon dioxide $^{13}CO_2$ to carbon dioxide $^{12}CO_2$.

According to this method, a predetermined volume of an exhalation of a patient is sucked into a gas inlet vessel and the pressure of the exhalation is measured to determine whether the amount of the exhalation collected in the breath bag is insufficient or not. Thus, the amount of the shortage of the exhalation can be determined with high accuracy. This can prevent output of data with poor reliability resulting from infrared spectrophotometry that is carried out with an insufficient amount of exhalation.

It is preferable that the maximum capacity volume of the breath bag is equal to or greater than the foregoing "predetermined volume" that is sucked into the gas inlet vessel. This is because if the maximum capacity volume of the breath bag is smaller than the foregoing "predetermined volume," the measured value of the pressure of the exhalation in the gas inlet vessel will always be below the atmospheric pressure and the measurement will be cancelled.

The arrangement may be such that after a predetermined volume of the exhalation collected in the breath bag is sucked into the gas inlet vessel, a valve is opened so that the gas inlet vessel is communicated with the inside of the cell that is maintained at the atmospheric pressure by being pre-filled with a prescribed gas, and the pressure of the gas after the communication is measured by a pressure sensor attached to the cell. In this case, measurement can be made utilizing the pressure sensor attached to the cell. Since the cell is usually provided with a pressure sensor, this pressure sensor can be utilized also for this purpose. Accordingly, it is not necessary to provide a pressure sensor directly attached to the foregoing gas inlet vessel, so that the structure of the apparatus can be simplified.

The aforementioned prescribed gas is generally a reference gas that does not absorb light having wavelengths at which light is transmitted through the respective component gases. This reference gas may be air. Alternatively, nitrogen gas may be used.

When the amount of the exhalation collected in the breath bag is judged to be insufficient, the exhalation in the gas inlet vessel is pressurized up to the atmospheric pressure, and the change in volume of the gas inlet vessel can be shown as the amount of shortage to the measurer. Thus, the measurer can refer to this when another exhalation is attempted.

An apparatus for exhaled gas measurement and analysis according to the present invention is an apparatus of an invention that is substantially equivalent to the foregoing method of exhaled gas measurement and analysis.

These and other advantages, features and effects of the present invention will become apparent from the following description of embodiments thereof with reference to the accompanying drawings.

DESCRIPTION OF THE REFERENCE SYMBOLS

Figure 1:
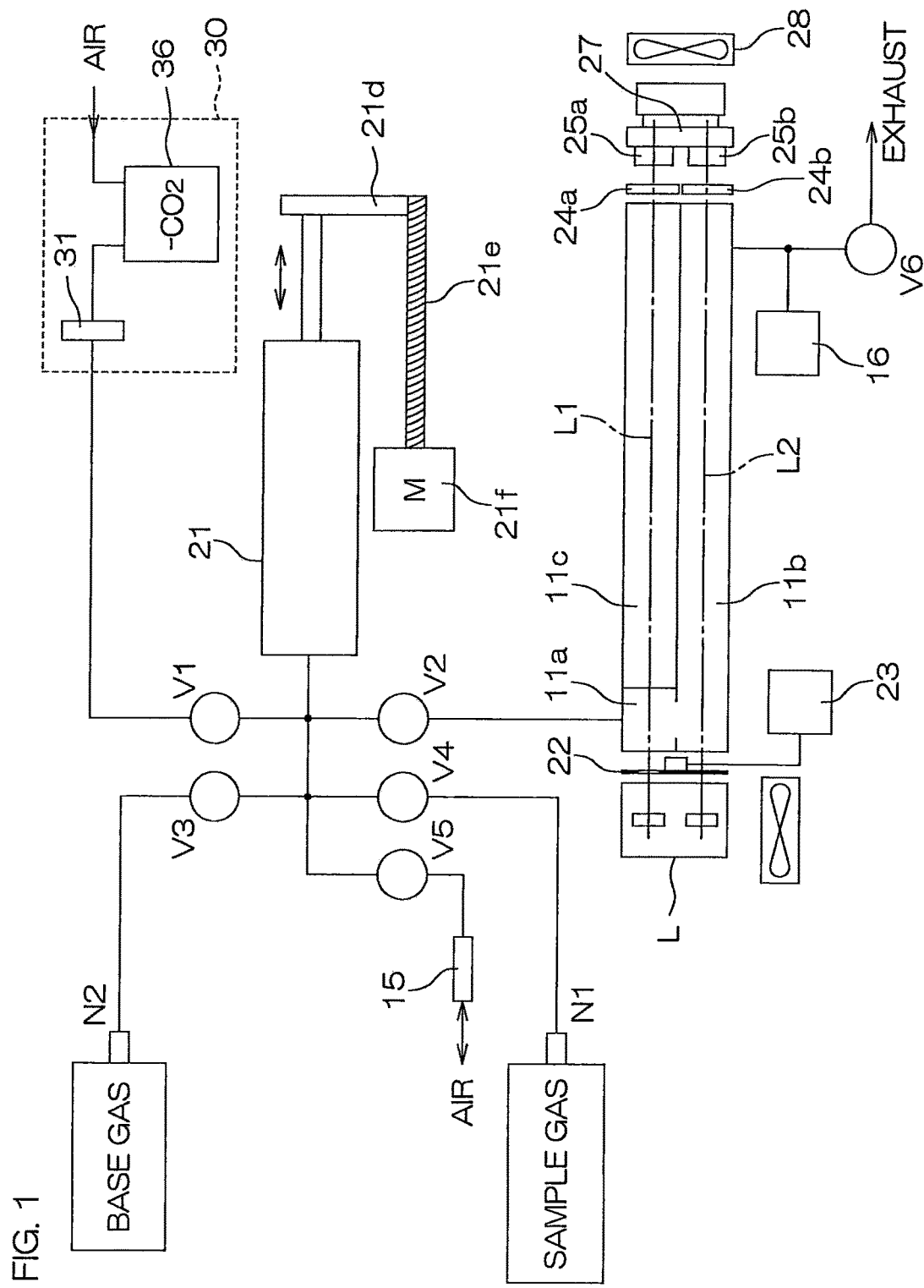
FIG. 1 is a block diagram showing an overall configuration of an apparatus for exhaled gas measurement and analysis of the present invention.

L Infrared light source device
N1, N2 Nozzle
V1-V6 Valve
11a First sample cell
11b Second sample cell
11c Dummy cell
15 Filter
16 Pressure sensor
21 Gas inlet vessel
21a Base board
21b Cylinder
24a First wavelength filter
24b Second wavelength filter
25a First detection device
25b Second detection device

BEST MODE FOR CARRYING OUT THE INVENTION

Hereinafter, an embodiment of the present invention where a urea diagnostic medicine marked with an isotope $^{13}C$ is administered to a human body, and the concentration of $^{13}CO_2$ in an exhalation of the patient is measured by infrared spectrophotometry will be described in detail referring to the accompanying drawings.

I. Breath Test

First, an exhalation of the patient before administration of the urea diagnostic medicine is collected in a breath bag. Then, the urea diagnostic medicine is administered orally. About 20 minutes after the administration, an exhalation of the patient is collected in the breath bag in the same way as before the administration.

The breath bag is capable of expanding and contracting and comprises a synthetic resin container with flexibility, a rubber container with elasticity, or the like. The breath bag can be inflated with an exhaled breath of the patient. The relationship between maximum volume VBag of exhalation that can be contained in the breath bag in the inflated state and volume Va to be sucked by the later described piston is expressed as follows:

$$VBag=(1+\beta)Va$$

Where $\beta$ represents a non-negative constant that is set in the range of $0 \leq \beta < \beta max$. The upper limit value $\beta max$ is a positive constant; for example, $\beta max=0.5$.

The respective breath bags before and after drug administration are set to predetermined nozzles of the exhaled gas measurement and analysis apparatus, and the following automatic measurements are performed.

II. Apparatus for Exhaled Gas Measurement and Analysis

FIG. 1 is a block diagram showing an overall configuration of an apparatus for exhaled gas measurement and analysis.

The breath bag in which the exhalation after drug administration (hereinafter referred to as "sample gas") is collected and the breath bag in which the exhalation before drug administration (hereinafter referred to as "base gas") is collected are set to a nozzle N1 and a nozzle N2, respectively. The nozzle N1 is connected to an electromagnetic valve (hereinafter simply referred to as "valve") V4 through a metal pipe (hereinafter simply referred to as "pipe"), and the nozzle N2 is connected to a valve V3 through a pipe. In addition, a valve V5 is connected to a pipe that takes in air through a dust filter 15.

Meanwhile, a reference gas (air from which $CO_2$ is removed is used here) supplied from a reference gas supply section 30 (later described) is led to a valve V1.

The valves V1, V3, V4 and V5 are connected to a gas inlet vessel 21 for quantitatively injecting the reference gas, sample gas or base gas. The gas inlet vessel 21 is a syringe-like device having a piston and a cylinder. The piston is driven by cooperation of a feed screw 21c connected to a pulse motor 21f and a nut 21d fixed to the piston (later described).

The gas inlet vessel 21 is linked to a first sample cell 11a and a second sample cell 11b via a valve V2.

A cell chamber 11 is constituted of, as shown in FIG. 1, the first sample cell 11a having a shorter length for measuring $12CO_2$ absorbance, the second sample cell 11b having a longer length for measuring $^{13}CO_2$ absorbance and a dummy cell 11c containing a gas that exhibits no absorption in the $CO_2$ absorption band. The first sample cell 11a is communicated with the second sample cell 11b, so that the gas introduced into the first sample cell 11a is introduced into the second sample cell 11b and exhausted through an exhaust valve V6.

A pressure sensor 16 for measuring gas pressure inside the first sample cell 11a and the second sample cell 11b is provided anterior to the exhaust valve V16. The type of detection of this pressure sensor 16 is not limited to any specific one, but may be of the kind that detects the motion of a diaphragm by a piezoelectric element.

The volume of the first sample cell 11a is about 0.085 ml, and the volume of the second sample cell 11b is about 3.915 ml. Specifically, the lengths of the first sample cell 11a, the second sample cell 11b and the dummy cell 11c are 5 mm, 140 mm and 135 mm, respectively. The cell chamber 11 is enclosed by a heat insulator (not shown).

The symbol L denotes an infrared radiation source device. The infrared radiation source device L includes two light sources for irradiating infrared beams. The generation of infrared radiation may be accomplished through any desired means, namely, a ceramic heater (surface temperature: 700° C.) and the like may be used. A chopper 22 for periodically blocking and passing the infrared beams is provided. The chopper 22 is rotated by a pulse motor 23.

A light path formed by a part of infrared beams radiated from the infrared radiation source device L that is transmitted through the first sample cell 11a and the dummy cell 11c is herein referred to as "first light path L1", while a light path formed by a part of the infrared beams that is transmitted through the second sample cell 11b is herein referred to as "second light path L2" (see FIG. 1).

An infrared beam detection device for detecting infrared beams that have been transmitted through the cells includes a first wavelength filter 24a and a first detection element 25a disposed in the first light path and a second wavelength filter 24b and a second detection element 25b disposed in the second light path.

The first wavelength filter 24a is designed to transmit an infrared beam with a wavelength of about 4280 nm that is the $^{12}CO_2$ absorbing wavelength band for measurement of the $^{12}CO_2$ absorbance, and the second wavelength filter 24b is designed to transmit an infrared beam with a wavelength of about 4412 nm that is the $^{13}CO_2$ absorbing wavelength band for measurement of the $^{13}CO_2$ absorbance. The first and second detection elements 25a and 25b are light receiving elements for detection of infrared beams and constituted of PIN diodes or the like.

The first wavelength filter 24a, the first detection element 25a, the second wavelength filter 24b and the second detection element 25b are maintained at a constant temperature by a temperature control block 27 using a Peltier element.

In addition, a fan 28 dissipates heat radiated from the Peltier element of the temperature control block to the outside of the apparatus.

Furthermore, a reference gas supply section 30 for supplying air from which $CO_2$ has been removed is attached to the main body of the apparatus for exhaled gas measurement and analysis. The reference gas supply section 30 includes a dust filter 31 and a carbon dioxide gas absorbing section 36 connected in series.

The carbon dioxide gas absorbing section 36 uses, for example, soda lime (a mixture of sodium hydroxide and calcium hydroxide) as carbon dioxide absorbent.

Figure 2:
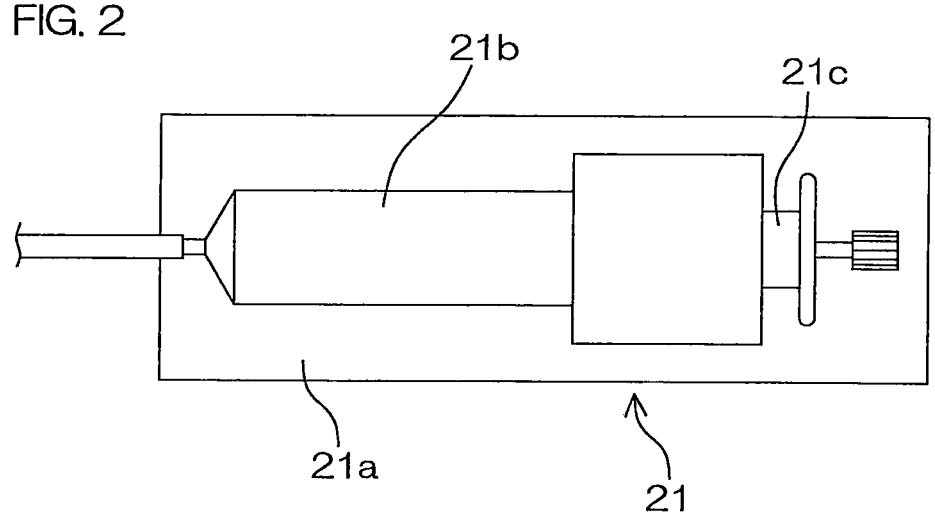
FIG. 2 is a plan view showing a gas inlet vessel for quantitatively injecting the gas to be measured.
Figure 3:
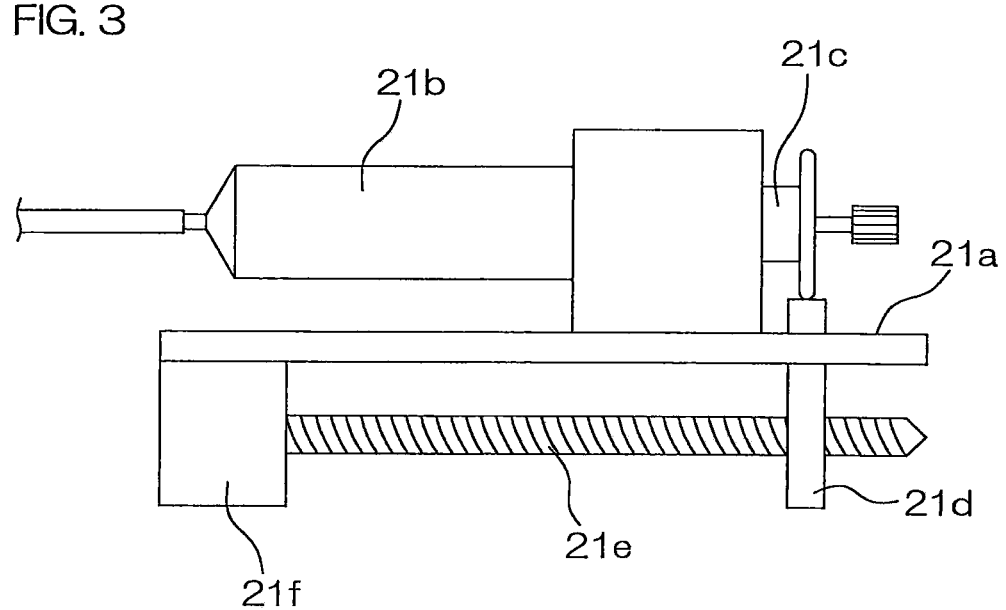
FIG. 3 is a front view of the gas inlet vessel.

FIGS. 2 and 3 are a plan view and a front view, respectively, showing the gas inlet vessel 21 for quantitatively injecting the gas to be measured.

The gas inlet vessel 21 has a construction including a base board 21a on which a cylinder 21b accommodating a piston 21c is disposed, and a movable nut 21d linked to the piston 21c, a feed screw 21e meshed with the nut 21d, and a pulse motor 21f for rotating the feed screw 21e that are provided under the base board 21a.

The foregoing pulse motor 21f is driven to rotate normally and reversely by a drive circuit not shown in the drawing. When the feed screw 21e is rotated by the rotation of the pulse motor 21f, the nut 21d moves back and forth according to the rotational direction, by which the piston 21c moves back and forth to any desired location. Thus, introduction of the gas to be measured into the cylinder 21b and discharge of the gas to be measured from the cylinder 21b can be freely controlled.

III. Measuring Procedure

The measuring procedure includes reference gas measurement, base gas measurement, reference gas measurement, sample gas measurement and reference gas measurement which are to be performed in this order. Now this is described referring to FIGS. 4-8. In these drawings, the arrows indicate flow of gas.

III-1. Reference Gas Measurement

Figure 4:
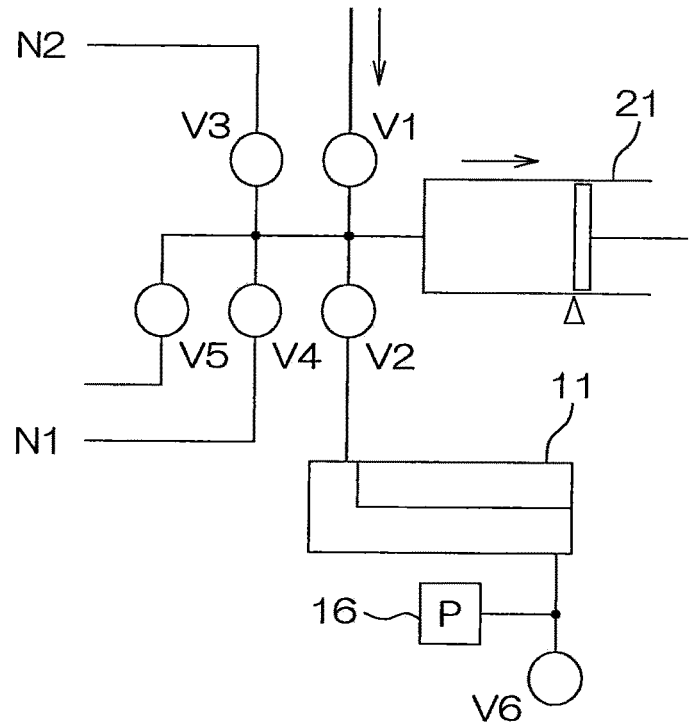
FIG. 4 shows a gas flow path in a reference measurement.

As shown in FIG. 4, the valve V1 is opened with the other valves closed, and a reference gas is sucked by means of the gas inlet vessel 21. At this time, the piston 21c is moved back and forth to clean the inside of the cylinder 21b.

Figure 5:
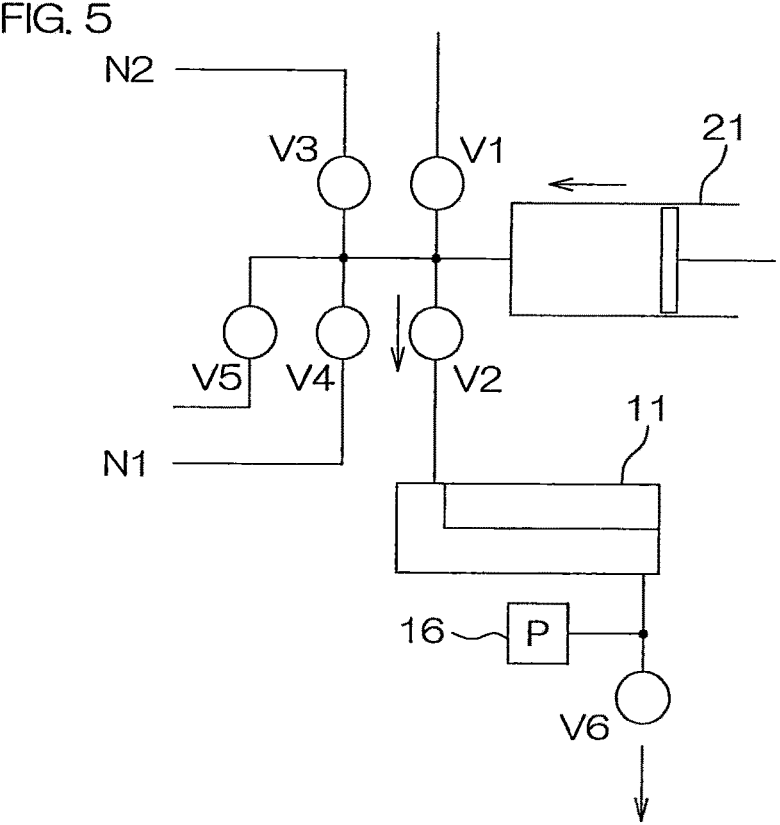
FIG. 5 shows a gas flow path in a reference measurement.

Then, as shown in FIG. 5, the valve V1 is closed and the valve V2 and the exhaust valve V6 are opened so that the reference gas inside the gas inlet vessel 21 is transferred into the first sample cell 11a and the second sample cell 11b. In this manner, a clean reference gas is flowed through the gas flow path and the cell chamber 11 to clean the gas flow path and the cell chamber 11.

Thereafter, the reference gas for measurement is injected from the gas inlet vessel 21 into the first sample cell 11a and the second sample cell 11b, and the intensities of light are measured by the respective detection elements 25a and 25b.

The light intensities thus obtained by the first detection element 25a and the second detection element 25b are represented by $^{12}R1$ and $^{13}R1$, respectively.

III-2. Base Gas Pressure Measurement

The base gas pressure measurement process will be described below referring to the process drawings of FIGS. 6-8 and the flowchart of FIG. 9.

Figure 6:
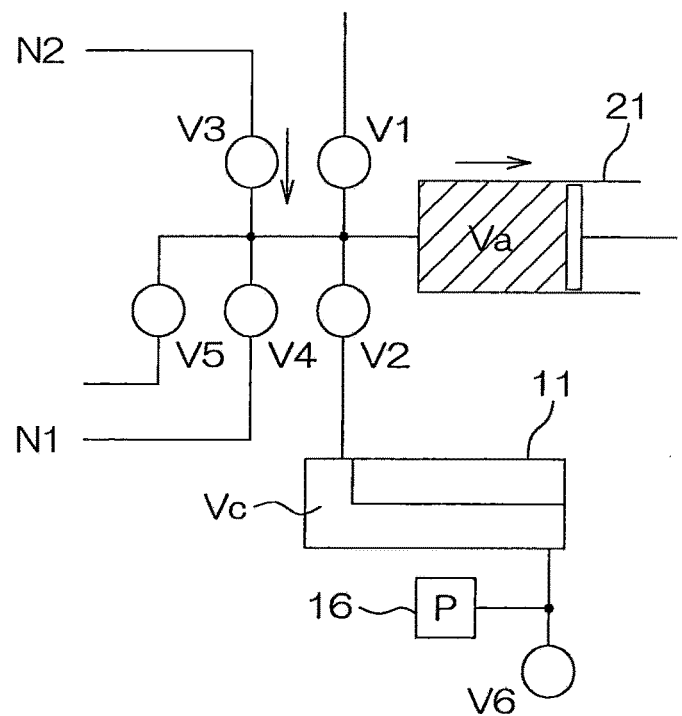
FIG. 6 shows a gas flow path in a gas pressure measurement.

As shown in FIG. 6, the valve V3 is opened with the other valves closed, the base gas inside the breath bag is sucked by means of the gas inlet vessel 21 with a volume Va required for the measurement, and the piston is stopped (Step S1). The volume Va is, for example, 35 ml.

Here, since the valves V2 and V6 are closed, the reference gas at the atmospheric pressure is retained inside the cell 11.

Figure 7:
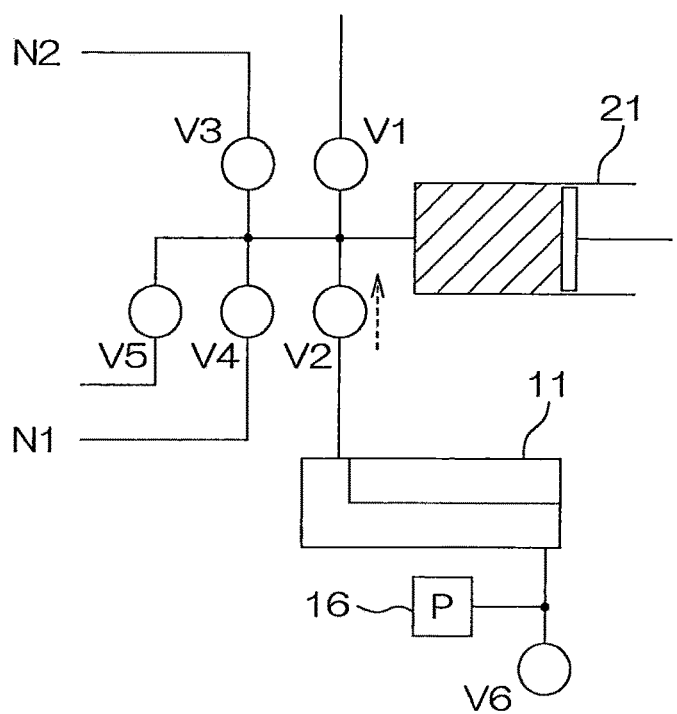
FIG. 7 shows a gas flow path in a gas pressure measurement.

Subsequently, as shown in FIG. 7, the valve V3 is closed and the valve V2 is opened so that the inside of the gas inlet vessel 21, the first sample cell 11a and the second sample cell 11b are communicated with each other.

That is, a hermetically closed space is formed by the inside of the gas inlet vessel 21, the first sample cell 11a and the second sample cell 11b. In this state, pressure is measured by the pressure sensor 16 (Step S2).

When the amount of the exhalation contained in the breath bag is less than the volume Va at the atmospheric pressure, the volume at the atmospheric pressure of the base gas that has been sucked by the gas inlet vessel 21 is less than Va, and the pressure inside the gas inlet vessel 21 is below the atmospheric pressure. When the valve V2 is opened, the reference gas inside the first sample cell 11a and the second sample cell 11b flows back to the gas inlet vessel 21. As a result, the gas pressure of the gas inlet vessel 21 and the first sample cell 11a as a whole becomes lower than the atmospheric pressure. This pressure value is read by the pressure sensor 16.

When the amount of the exhalation contained in the breath bag is not less than the volume Va at the atmospheric pressure, the volume at the atmospheric pressure of the base gas sucked by the gas inlet vessel 21 is Va. The inside of the gas inlet vessel 21 is kept at the atmospheric pressure, and when the valve V2 is opened, the pressure of the gas including the reference gas inside the first sample cell 11a and the second sample cell 11b is also the atmospheric pressure.

This is summarized as follows: when the base gas that can be sucked from the breath bag into the gas inlet vessel 21 is as much as the volume Va at the atmospheric pressure, the pressure measured by the pressure sensor 16 is the atmospheric pressure, while the pressure measured by the pressure sensor 16 is below the atmospheric pressure when the gas inlet vessel 21 fails to suck as much base gas as the volume Va at the atmospheric pressure from the breath bag.

In this case, since pressure measurements are conducted inside the hermetically closed space, influences from the outside environment can be eliminated, so that pressure measurements with high accuracy can be accomplished. Therefore, shortage of the exhalation can be detected accurately even if the amount of the shortage is small.

A value measured by the pressure sensor 16 less than the atmospheric pressure indicates that the amount of the base gas contained in the breath bag is less than the amount necessary for the measurement. In this case, the amount of shortage of the base gas is measured.

Figure 8:
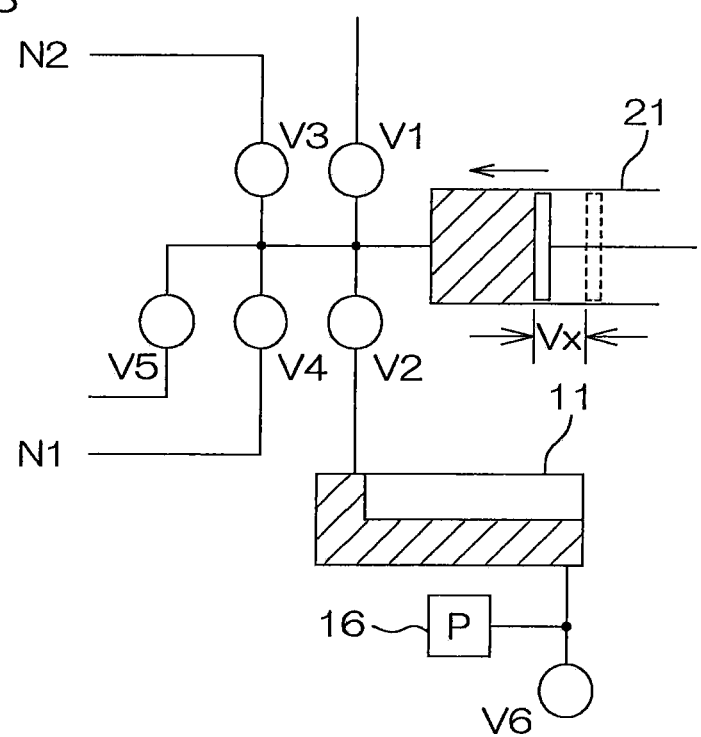
FIG. 8 shows a gas flow path in a gas pressure measurement.
Figure 9:
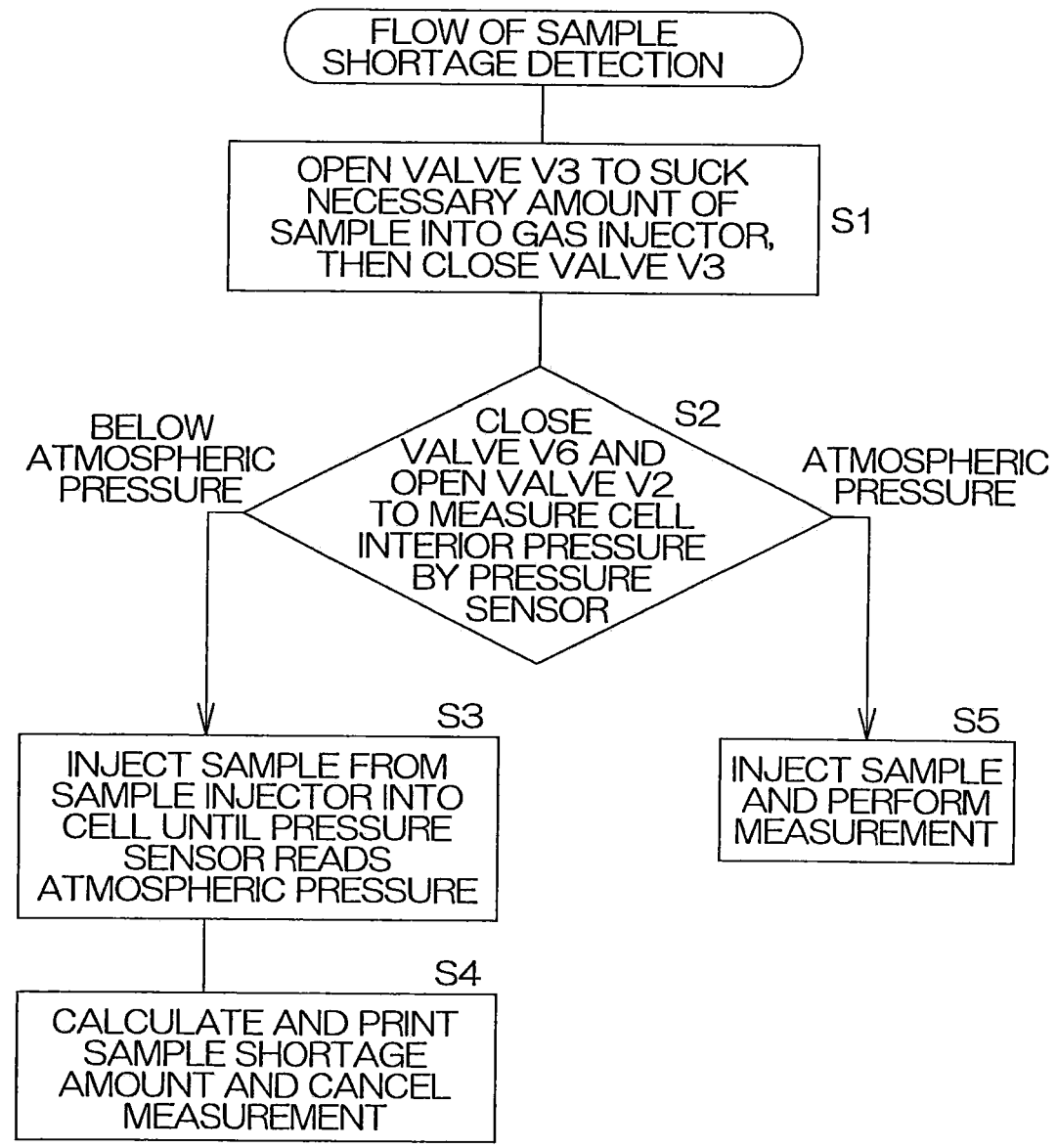
FIG. 9 is a flowchart showing the steps of a base gas pressure measurement process.

That is, as shown in FIG. 8, the valve V2 is opened and the other valves are closed, and while the pressure is measured by the pressure sensor 16, the base gas is transferred from the gas inlet vessel 21 to the first sample cell 11a and the second sample cell 11b (Step S3).

When the value read by the pressure sensor 16 reaches the atmospheric pressure, the operation of the gas inlet vessel 21 is stopped.

In this state, a volume Vx corresponding to the displacement of the piston of the gas inlet vessel 21 is measured.

This Vx represents the amount of shortage of the base gas.

Then, the display (not shown) shows an indication of cancellation of the measurement together with the volume of the base gas necessary to fill the shortage. Then, further processing of the base gas measurement is cancelled (Step S4).

The indication of the display notifies the measurer of the shortage of the base gas, the cancellation of the measurement, as well as the amount of the base gas shortage. This massage will be conveyed to the patient, making the patient reattempt to fill the breath bag with the base gas.

When the value measured by the pressure sensor 16 is the atmospheric pressure, the processing proceeds to the next step of base gas measurement (Step S5).

III-3. Base Gas Measurement

Figure 10:
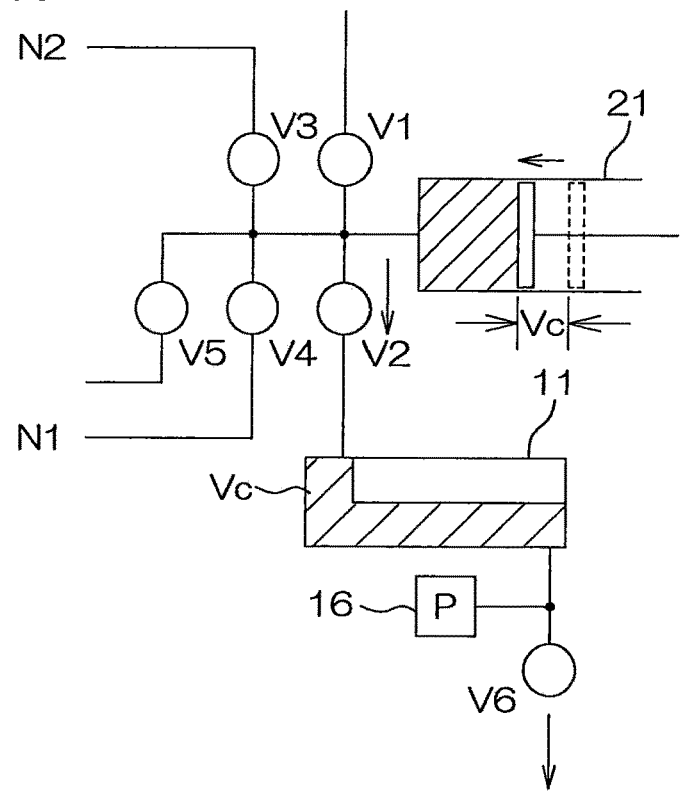
FIG. 10 shows a gas flow path in a light intensity measurement.

As shown in FIG. 10, the valves V2 and V6 are opened with the other valves closed, and the base gas is mechanically pushed out by means of the gas inlet vessel 21 with a volume corresponding to Vc (in this case 4 ml). By this operation, the reference gas in the first sample cell 11a and the second sample cell 11b is replaced by the base gas.

Figure 11:
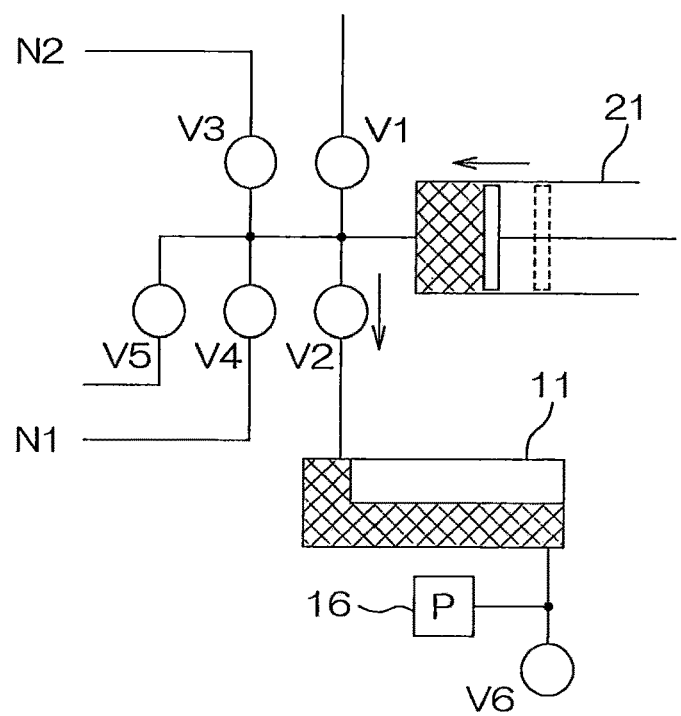
FIG. 11 shows a gas flow path in a light intensity measurement.

In this state, the valve V6 is closed and the piston is moved as shown in FIG. 11. Since the exhaust valve V6 is kept closed, the insides of the gas inlet vessel 21, the first sample cell 11a and the second sample cell 11b are pressurized.

The pressure inside the first sample cell 11a and the second sample cell 11b is measured by the pressure sensor 16. The measured pressure value is represented by P. When the value of P becomes a predetermined pressure P0, for example, 4 atmospheric pressure, the movement of the piston is stopped and the valve V2 is closed, and then the intensities of light are measured. The light intensities thus obtained by the first detection element 25a and the second detection element 25b are represented by $^{12}$B and $^{13}$B, respectively.

III-4. Reference Measurement

Then, cleaning of the gas flow path and the cell and light intensity measurement of the reference gas are performed again (see FIG. 4(b)). The light intensities thus obtained by the first detection element 25a and the second detection element 25b are represented by $^{12}$R2 and $^{13}$R2, respectively.

III-5. Sample Gas Pressure Measurement

The same measurement as the pressure measurement described in III-2 above is performed, except that a breath bag containing a sample gas instead of the base gas is set to the nozzle N1, and the valve V4 is opened/closed instead of the valve V3.

When the sample gas with a volume of Va at the atmospheric pressure can be sucked from the breath bag, the processing proceeds to the next step of sample gas measurement.

When the sample gas with a volume of Va at the atmospheric pressure cannot be sucked from the breath bag, it means that the amount of the sample gas contained in the breath bag is less than the amount necessary for the measurement. In this case, the amount of the shortage of the sample gas is measured, and the display (not shown) shows an indication of cancellation of the measurement together with the volume of the sample gas necessary to fill the shortage. Then, further processing is cancelled.

The indication of the display notifies the measurer of the shortage of the base gas and the cancellation of the measurement. This massage will be conveyed to the patient, making the patient reattempt to fill the breath bag with the sample gas.

III-6. Sample Gas Measurement

Light intensity measurement for the sample gas is carried out through the same procedure as in the base gas measurement described in III-3.

That is, the valves V2 and V6 are opened with the other valves closed, and the sample gas is mechanically pushed out by means of the gas inlet vessel 21 with a volume corresponding to Vc (in this case, 4 ml), by which the reference gas in the first sample cell 11a and the second sample cell 11b is replaced by the sample gas.

In this state, the valve V6 is closed and the piston is moved, thereby pressurizing the insides of the first sample cell 11a and the second sample cell 11b.

When the pressure inside the first sample cell 11a and the second sample cell 11b measured by the pressure sensor 16 becomes the predetermined pressure P0, for example, 4 atmospheric pressure, the movement of the piston is stopped, and in this state the valve V2 is closed, and then the light intensities are measured by the respective detection elements 25a and 25b.

The light intensities thus obtained by the first detection element 25a and the second detection element 25b are represented by $^{12}$S and $^{13}$S, respectively.

III-7. Reference Measurement

Then, cleaning of the gas flow path and the cell and light intensity measurement for the reference gas are performed again (see FIG. 4).

The light intensities thus obtained by the first detection element 25a and the second detection element 25b are represented by $^{12}$R3 and $^{13}$R3, respectively.

IV. Data Processing

IV-1. Calculation of Base Gas Absorbance

First, both an absorbance $^{12}$Abs(B) of $^{12}CO_2$ and an absorbance $^{13}$Abs(B) of $^{13}CO_2$ in the base gas are calculated with the use of the transmitted light intensities $^{12}R1$, $^{13}R1$ of the reference gas, the transmitted light intensities $^{12}B$, $^{13}B$ of the base gas, and the transmitted light intensities $^{12}R2$, $^{13}R2$ of the reference gas.

Here, the absorbance $^{13}$Abs(B) of $^{12}CO_2$ is obtained by the following equation:

$$^{12}Abs(B) = -\log[2 \cdot {}^{12}B/({}^{12}R1 + {}^{12}R2)]$$

The absorbance $^{13}$Abs(B) of $^{13}CO_2$ is obtained by the following equation:

$$^{13}Abs(B) = -\log[2 \cdot {}^{13}B/({}^{13}R1 + {}^{13}R2)]$$

Thus, when calculating each absorbance, the average value (R1+R2)/2 of the light intensities obtained by the earlier and later reference measurements is calculated, and the absorbance is then calculated with the use of the average value thus obtained and the light intensities obtained by the base gas measurement. Accordingly, the influence of drift (influence exerted on measurement by the passage of time) can be cancelled. Therefore, the measurement can quickly be initiated without the need of waiting until the apparatus is brought into perfect thermal equilibrium at the start up thereof (generally, several hours are required).

IV-2. Calculation of Sample Gas Absorbance

Then, both an absorbance $^{12}$Abs(S) of $^{12}CO_2$ and an absorbance $^{13}$Abs(S) of $^{13}CO_2$ in the sample gas are calculated with the use of the transmitted light intensities $^{12}R2$, $^{13}R2$ of the reference gas, the transmitted light intensities $^{12}S$, $^{13}S$ of the sample gas, and the transmitted light intensities $^{12}R3$, $^{13}R2$ of the reference gas.

Here, the absorbance $^{13}$Abs(S) of $^{12}CO_2$ is obtained by the following equation:

$$^{13}Abs(S) = -\log[2 \cdot {}^{12}S/({}^{12}R2 + {}^{12}R3)]$$

The absorbance $^{13}$Abs(S) of $^{13}CO_2$ is obtained by the following equation:

$$^{13}Abs(S) = -\log[2 \cdot {}^{13}S/({}^{13}R2 + {}^{13}R3)]$$

Thus, when calculating each absorbance, the average value of the light intensities obtained by the earlier and later reference measurements is calculated, and the absorbance is then calculated with the use of the average value thus obtained and the light intensities obtained by the sample gas measurement. Accordingly, the influence of drift can be cancelled.

IV-3. Concentration Calculation

Carbon dioxide $^{13}CO_2$ concentration and carbon dioxide $^{12}CO_2$ concentration are obtained with the use of calibration curves that define the relationship between absorbance and concentration of carbon dioxide $^{13}CO_2$ and $^{12}CO_2$.

The calibration curves are prepared with the use of a gas to be measured of which $^{12}CO_2$ concentration is known and a gas to be measured of which $^{13}CO_2$ concentration is known.

The calibration curves are assumed to be produced at a predetermined pressure (e.g. 4 atmospheric pressure). Data of the relationship between absorbance and concentration in the calibration curves and the value of pressure P0 are stored in the analysis computer included in the apparatus for exhaled gas measurement and analysis.

To obtain a calibration curve, $^{12}CO_2$ absorbances are measured for $^{12}CO_2$ concentrations changed in the range of about 0%-8%. The data thus obtained are plotted with $^{12}CO_2$ concentration as the abscissa and $^{12}CO_2$ absorbance as the ordinate. Then, the curve is determined by the method of least squares.

To obtain a calibration curve for $^{13}CO_2$, $^{13}CO_2$ absorbances are measured for $^{13}CO_2$ concentrations changed in the range of about 0%-0.08%. The data thus obtained are plotted with $^{13}CO_2$ concentration as the abscissa and $^{13}CO_2$ absorbance as the ordinate. Then, the curve is determined by the method of least squares.

The curves approximated by quadratic equations are relatively less in error. Accordingly, the calibration curves approximated by quadratic equations are adopted in this embodiment.

The respective concentration data obtained using the calibration curves above are represented as follows: the $^{12}CO_2$ concentration of the base gas is represented by $^{12}$Conc(B), the $^{13}CO_2$ concentration of the base gas by $^{13}$Conc(B), the $^{12}CO_2$ concentration of the sample gas by $^{12}$Conc(S), and the $^{13}CO_2$ concentration of the sample gas by $^{13}$Conc(S).

IV-4. Calculation of Concentration Ratio

Then, concentration ratio between $^3CO_2$ and $^{12}CO_2$ is determined. The concentration ratio of the base gas is obtained by:

$$^{13}\text{Conc}(B)/^{12}\text{Conc}(B)$$

The concentration ratio of the sample gas is obtained by:

$$^{13}\text{Conc}(S)/^{12}\text{Conc}(S)$$

Additionally, the concentration ratios may also be defined as $^{13}$Conc(B)/($^{12}$Conc(B)+$^{13}$Conc(B)), and $^{13}$Conc(S)/($^{12}$Conc(S)+$^{13}$Conc(S)). Since the $^{12}CO_2$ concentrations are much greater than the $^{13}CO_2$ concentrations, almost identical results are obtained in either way.

IV-5. Determination of $^{13}C$ Change

A $^{13}C$ difference between the sample gas and the base gas is calculated from the following equation:

$$\Delta^{13}C = [\text{Concentration ratio of sample gas} - \text{Concentration ratio of base gas}] \times 10^3 / [\text{Concentration ratio of base gas}] \text{ (Unit: per mill (per thousand))}$$

EXAMPLE

An examination was conducted to see whether the relationship between the amounts of shortage of base gas or sample gas (hereinafter collectively referred to as "specimen gas") inside the gas inlet vessel 21 and the pressure values read by the pressure sensor 16 is determined accurately.

First, 24 breath bags were prepared and separated into 3 groups each including 8 breath bags.

A specimen gas was injected into the 8 bags of each group in different amounts of 34, 33, 32, . . . 10, 0 ml as shown in the column of "SPECIMEN AMOUNT" of Table 1.

The volume Va of the specimen gas to be sucked from the gas inlet vessel 21 was 35 ml.

Accordingly, the gas shortage amounts were 1, 2, 3, . . . , 25, 35 ml, respectively, as shown in Table 1.

Three exhaled gas measurement and analysis apparatuses No. 1, No. 2 and No. 3 were prepared.

In the exhaled gas measurement and analysis apparatus No. 1, the specimen gas was sucked from the breath bags into the gas inlet vessel 21, and then with the valve V2 being opened, the pressure inside the cell was measured by the pressure sensor 16. As a result, the cell interior pressure data as shown in Table 1 were obtained. Each cell interior pressure is shown by the difference from 1 atmospheric pressure (unit: MPa).

Also in the other exhaled gas measurement and analysis apparatuses No. 2 and No. 3, the specimen gas was sucked from the breath bags into the gas inlet vessel 21, and then with the valve V2 being opened, the pressure inside the cell was measured by the pressure sensor 16. As a result, the cell interior pressure data as shown in Table 1 were obtained.

Average values of cell interior pressures of the three exhaled gas measurement and analysis apparatuses where the amounts of the specimen gas shortage were the same were calculated. As a result, average values of the cell interior pressures and the respective standard deviation data were obtained as shown in Table 1.

TABLE 1

| SPECIMEN AMOUNT (ml) | SPECIMEN SHORTAGE (ml) | CELL INTERIOR PRESSURE | | | AVERAGE CELL INTERIOR PRESSURE | Unit: MPa<br>STANDARD DEVIATION |
|---|---|---|---|---|---|---|
| | | NO. 1 | NO. 2 | NO. 3 | | |
| 34 | 1 | −0.003 | −0.002 | −0.002 | −0.002 | 0.00058 |
| 33 | 2 | −0.006 | −0.005 | −0.005 | −0.005 | 0.00058 |
| 32 | 3 | −0.008 | −0.007 | −0.007 | −0.007 | 0.00058 |
| 31 | 4 | −0.010 | −0.010 | −0.009 | −0.010 | 0.00058 |
| 30 | 5 | −0.012 | −0.013 | −0.011 | −0.012 | 0.00100 |
| 20 | 15 | −0.033 | −0.035 | −0.034 | −0.034 | 0.00100 |
| 10 | 25 | −0.056 | −0.055 | −0.054 | −0.055 | 0.00100 |
| 0 | 35 | −0.078 | −0.077 | −0.077 | −0.077 | 0.00058 |

Figure 12:
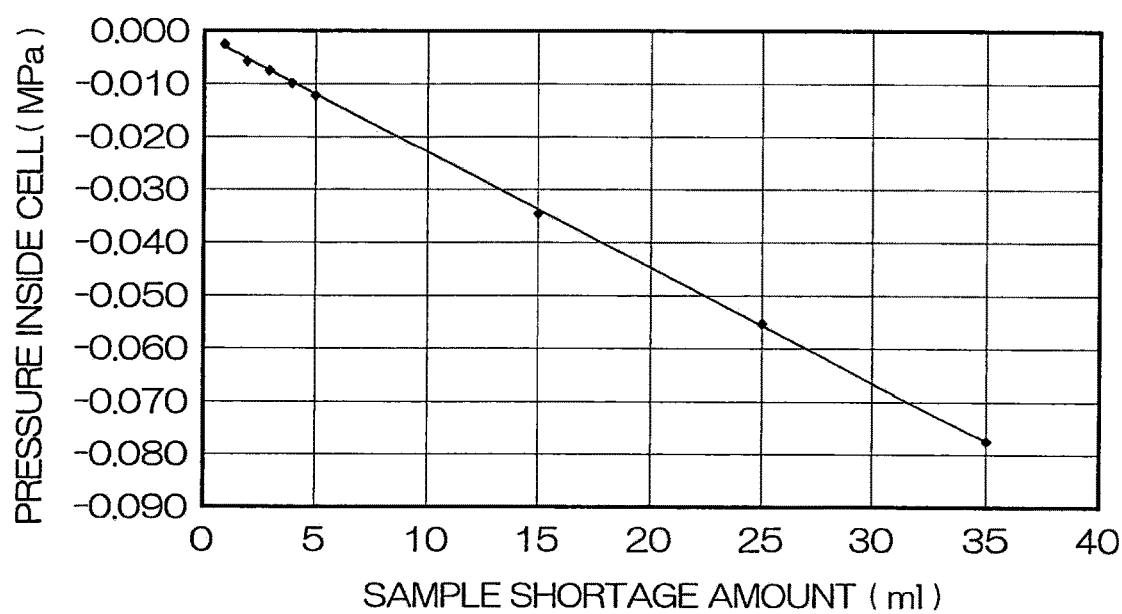
FIG. 12 is a graph in which cell interior pressure average is plotted with respect to amount of shortage of sample gas in Example.

These cell interior pressure average data were plotted with respect to the specimen shortage amounts as shown in FIG. 12.

As is apparent from this graph, the straight line shows that the cell interior pressure average with respect to the specimen gas shortage amount is reproduced with high accuracy. In addition, the values of standard deviation are small.

It is therefore verified that determination of shortage of the specimen gas can be made with high accuracy by the present invention.

The invention claimed is:

1. A method of cancelling an exhaled gas measurement and analysis where the amount of exhaled gas is insufficient and determining the amount of shortage comprising the steps of:

collecting an exhalation of a human body including carbon dioxide $^{13}CO_2$ and carbon dioxide $^{12}CO_2$ as component gases into a breath bag capable of expanding and contracting;

sucking a predetermined volume of the exhalation collected in the breath bag into a gas inlet vessel;

measuring a pressure of the exhalation in the gas inlet vessel and determining it is below an atmospheric pressure;

pressurizing the exhalation inside the gas inlet vessel up to the atmospheric pressure;

showing on a display an indication of cancellation of the measurement together with the volume of the exhaled gas necessary to fill the shortage; and cancelling further processing.

* * * * *